United States Patent [19]

Kristinsson

[11] Patent Number: 4,931,439
[45] Date of Patent: Jun. 5, 1990

[54] PESTICIDES

[75] Inventor: Haukur Kristinsson, Basel, Switzerland

[73] Assignee: Ciba-Geigy Corporation, Ardsley, N.Y.

[21] Appl. No.: 255,684

[22] Filed: Oct. 11, 1988

[30] Foreign Application Priority Data

Oct. 16, 1987 [CH] Switzerland .................. 4062/87

[51] Int. Cl.⁵ ................. A01N 43/707; C07D 253/06; C07D 253/08
[52] U.S. Cl. .................................. 514/242; 514/243; 544/182; 544/183
[58] Field of Search ............... 544/182, 183; 514/242, 514/243

[56] References Cited

FOREIGN PATENT DOCUMENTS 1795785 8/1975 Fed. Rep. of Germany.

OTHER PUBLICATIONS

Liebigs Annalen der Chemie. 749, pp. 125-133 (1971) [Hetzheim et al.].

Primary Examiner—John M. Ford
Attorney, Agent, or Firm—Kevin T. Mansfield

[57] ABSTRACT

Novel substituted N-amino-1,2,4-triazinones of formula I

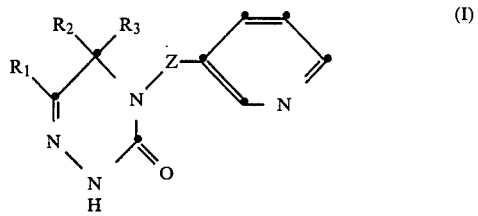

wherein
$R_1$ is hydrogen, $C_1$-$C_{12}$alkyl, $C_3$-$C_6$cycloalkyl, $C_1$-$C_4$alkoxy-$C_1$-$C_6$alkyl, $C_1$-$C_2$haloalkyl, phenyl, benzyl, phenethyl, phenproptyl, phenbutyl or phenpentyl, or a phenyl, benzyl, phenethyl, phenpropyl, phenbutyl or phenpentyl radical that is mono- or di-substituted by halogen, $C_1$-$C_5$-alkyl, $C_1$-$C_2$haloalkyl, methoxy and/or by ethoxy,
$R_2$ is hydrogen, $C_1$-$C_6$alkyl or $C_3$-$C_6$ cycloalkyl, or is phenyl that is unsubstituted or substituted by $C_1$-$C_{12}$alkyl, halogen or by $C_1$-$C_{12}$haloalkyl, or $R_1$ and $R_2$ together form a saturated or unsaturated 3- to 7-membered carbocycle,
$R_3$ is hydrogen or $C_1$-$C_6$ alkyl and
Z is —N=CH— or —NH—CH$_2$—, and their salts with organic or inorganic acids, processes and intermediates for their preparation, and their use in pest control and in pesticidal copositions that contain a compound of formula I as active ingredient are disclosed. The preferred field of application is the control of pests in and on animals and plants.

14 Claims, No Drawings

PESTICIDES

The present invention relates to novel insecticidally active N-amino-1,2,4-triazinones, processes and intermediates for their preparation, compositions containing these aminotriazinones, and their use in pest control.

The aminotriazinones according to the invention correspond to formula I

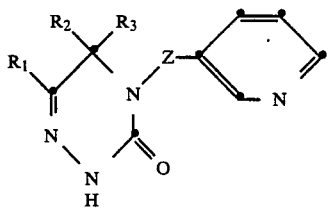

wherein
$R_1$ is hydrogen, $C_1-C_{12}$alkyl, $C_3-C_6$cycloalkyl, $C_1-C_4$-alkoxy-$C_1-C_6$alkyl, $C_1-C_2$haloalkyl, phenyl, benzyl, phenethyl, phenpropyl, phenbutyl or phenpentyl, or a phenyl, benzyl, phenethyl, phenpropyl, phenbutyl or phenpentyl radical that is mono- or di-substituted by halogen, $C_1-C_5$alkyl, $C_1-C_2$haloalkyl, methoxy and/or by ethoxy,
$R_2$ is hydrogen, $C_1-C_6$alkyl or $C_3-C_6$cycloalkyl, or is phenyl that is unsubstituted or substituted by $C_1-C_{12}$alkyl, halogen or by $C_1-C_{12}$haloalkyl, or $R_1$ and $R_2$ together form a saturated or unsaturated 3- to 7-membered carbocycle,
$R_3$ is hydrogen or $C_1-C_6$alkyl and
Z is —N=CH— or —NH—CH$_2$—.

The compounds of formula I can also be in the form of acid addition salts. Both organic and inorganic acids are suitable for the formation of such salts. Examples of such acids are, inter alia, hydrochloric acid, hydrobromic acid, nitric acid, various phosphoric acids, sulfuric acid, acetic acid, propionic acid, butyric acid, valeric acid, oxalic acid, malonic acid, maleic acid, fumaric acid, lactic acid, tartaric acid or salicylic acid.

The alkyl radicals that are suitable as substituents may be straight-chained or branched. Examples of such alkyl radicals are methyl, ethyl, propyl, isopropyl, butyl, isobutyl, sec.-butyl, tert.-butyl or pentyl, hexyl, octyl, decyl, dodecyl, etc. and their isomers.

The alkoxyalkyl radicals that are suitable as substituents may be straight-chained or branched, the alkyl and alkoxy radicals being as defined above. Suitable examples of such substituents are, inter alia, methoxymethyl, methoxyethyl, ethoxyethyl, methoxypropyl, ethoxypropyl, propoxypropyl, methoxybutyl, ethoxybutyl, propoxybutyl or butoxybutyl.

The cycloalkyl radicals that are suitable as substituents are, for example, cyclopropyl, cyclobutyl, cyclopentyl or cyclohexyl.

The halogen atoms that are suitable as substituents are fluorine and chlorine and also bromine and iodine, fluorine and chlorine being preferred.

The halogenated $C_1-C_2$alkyl radicals that are suitable as substituents may be only partially halogenated or may be perhalogenated, the halogen atoms being as defined above. Especially suitable examples of such substituents are, inter alia, methyl mono- to tri-substituted by fluorine, chlorine and/or by bromine, for example $CHF_2$ or $CF_3$; and ethyl mono- to penta-substituted by fluorine, chlorine and/or by bromine, for example $CH_2CF_3$, $CF_2CF_3$, $CF_2CCl_3$, $CF_2CHCl_2$, $CF_2CHF_2$, $CF_2CHBr_2$, $CF_2CHClF$, $CF_2CHBrF$ or $CClFCHClF$.

The 3- to 7-membered carbocycles formed by $R_1$ and $R_2$ may be saturated or unsaturated. They are preferably saturated 5- or 6-membered carbocycles.

Of the compounds of formula I, prominence should be given to those wherein $R_1$ is hydrogen, $C_1-C_6$alkyl, $C_3-C_5$cycloalkyl, phenyl or phenyl that is mono- or di-substituted by halogen, $C_1-C_3$alkyl, methoxy or by ethoxy; each of $R_2$ and $R_3$ is hydrogen or $C_1-C_4$alkyl and Z is —N=CH— or —NH—CH$_2$—.

Of the above, the compounds of formula I that are preferred are those wherein
(a) $R_1$ is hydrogen, $C_1-C_4$alkyl, cyclopropyl or phenyl; $R_2$ is hydrogen, methyl or ethyl; $R_3$ is hydrogen or methyl; and Z is —N=CH— or
(b) $R_1$ is hydrogen, $C_1-C_4$alkyl, cyclopropyl or phenyl; $R_2$ is hydrogen, methyl or ethyl; $R_3$ is hydrogen or methyl; and Z is —NH—CH$_2$—.

The compounds of formula I according to the invention can be prepared in accordance with processes that are known in principle, for example by
(A) reacting an aminotriazinone of formula II

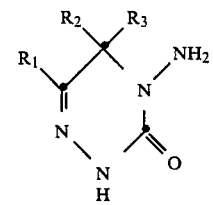

with an aldehyde of formula III

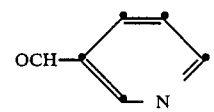

and, if desired,
(B) converting the resulting pyridyl-methyleneamino-triazinone of formula Ia

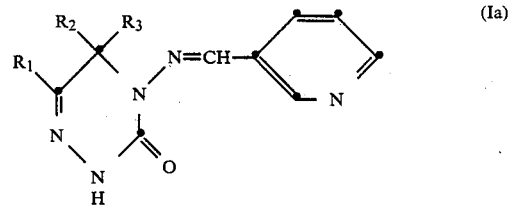

by selective reduction into the pyridyl-methylaminotriazinone of formula Ib

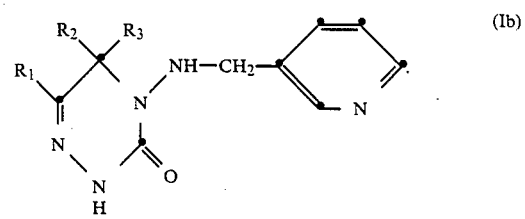

In the above formulae, $R_1$, $R_2$ and $R_3$ are as defined hereinbefore.

Process A is generally carried out under normal pressure in the presence of a catalytic amount of a strong acid and in a solvent. The reaction temperature is from +10° to 100° C., preferably from +40° to 80° C. Suitable acids are strong inorganic acids, for example mineral acids, especially hydrochloric acid. Suitable solvents are alcohols, ethers and ethereal compounds, nitriles or, alternatively, water.

Process B is generally carried out under normal or slightly elevated pressure in the presence of a suitable hydrogenation catalyst and in a solvent. Suitable hydrogenation catalysts are the customary platinum, palladium or nickel catalysts, for example Raney nickel, or also hydrides, for example sodium borohydride. Suitable solvents are alcohols, acetic acid, ethyl acetate or, alternatively, water.

The aminotriazinones of formula II can be prepared, for example, by a ring rearrangement using hydrazine hydrate by reacting an oxadiazolone of formula IV

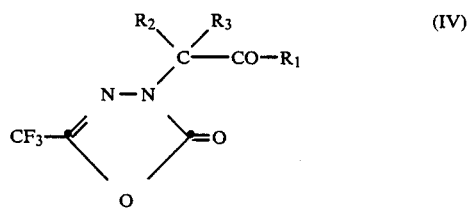

with hydrazine hydrate ($H_2N-NH_2.H_2O$), $R_1$, $R_2$ and $R_3$ being as defined for formula I.

The process for the preparation of the aminotriazinones of formula II is generally carried out under normal pressure and, if desired, in a solvent. The temperature is from +15° to 120° C., preferably from +20° to 80° C. Suitable solvents are, inter alia, water, nitriles, such as acetonitrile, alcohols, dioxane or tetrahydrofuran.

The oxadiazolones of formula IV can be prepared in accordance with processes that are known in principle, for example by reacting the 5-trifluoromethyl-1,3,4-oxadiazol-2(3H)-one of formula V

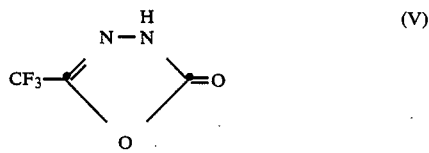

with a ketone of formula VI

$R_1$, $R_2$ and $R_3$ being as defined for formula I and X being halogen.

The process for the preparation of the oxadiazolones of formula IV is carried out under normal pressure in the presence of a base and in a solvent. The temperature is from 0° to +150° C., preferably from +20° to 100° C. Suitable bases are organic and inorganic bases, for example trimethylamine, alcoholates, sodium hydroxide or sodium hydride. Suitable solvents are, inter alia, alcohols, halogenated hydrocarbons, for example chloroform, nitriles, for example acetonitrile, tetrahydrofuran, dioxane, dimethyl sulfoxide or, alternatively, water.

Of the aminotriazinones of formula II, 4-amino-6-phenyl-1,2,4-triazin-3-one is known (Liebigs Annalen der Chemie, 749, 125 (1971)), that is to say, the compound of formula II wherein $R_1$ is phenyl and each of $R_2$ and $R_3$ is hydrogen. All the other compounds of formula II, that is to say the compounds of formula IIa

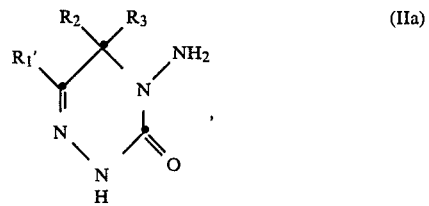

wherein $R_1'$ is hydrogen, $C_1$–$C_{12}$alkyl, $C_3$–$C_6$cycloalkyl, $C_1$–$C_4$alkoxy-$C_1$–$C_6$alkyl, $C_1$–$C_2$haloalkyl, benzyl, phenethyl, phenpropyl, phenbutyl or phenpentyl, or a phenyl, benzyl, phenethyl, phenpropyl, phenbutyl or phenpentyl radical that is mono- or di-substituted by halogen, $C_1$–$C_5$alkyl, $C_1$–$C_2$-haloalkyl, methoxy and/or by ethoxy, $R_2$ is hydrogen, $C_1$–$C_6$alkyl or $C_3$–$C_6$cycloalkyl, or is phenyl that is unsubstituted or substituted by $C_1$–$C_{12}$alkyl, halogen or by $C_1$–$C_{12}$haloalkyl, or $R_1$ and $R_2$ together form a saturated or unsaturated 3- to 7-membered carbocycle, $R_3$ is hydrogen or $C_1$–$C_6$alkyl, and the oxadiazolones of formula IV are novel and the invention relates also to these.

The compounds of formulae III, V and VI are known or can be prepared in accordance with processes that are known in principle.

It has been found that the compounds of formula I according to the invention, at the same time as being well tolerated by plants, are better tolerated by warm-blooded animals and have a greater stability than known phosphoric acid esters and carbamates. They are therefore eminently suitable as pesticides, especially for controlling pests, especially insects, that attack plants and animals.

The compounds of formula I are suitable especially for controlling insects of the orders Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera and also representatives of the order Acarina.

With the aid of the compounds of formula I used according to the invention it is possible to control especially plant-destructive insects, especially plant-destructive insects in crops of ornamental and useful plants, especially in cotton crops, vegetable crops, rice crops and fruit crops. In this connection, attention is drawn to the fact that the said compounds are distinguished both by a very pronounced systemic action and also contact action against sucking insects, especially against insects of the Aphididae family (for example *Aphis fabae, Aphis craccivora* and *Myzus persicae*) that can be controlled by conventional pesticides only with difficulty.

The good pesticidal activity of the compounds of formula I proposed according to the invention corresponds to a mortality of at least from 50 to 60% of the pests mentioned.

The activity of the compounds used according to the invention or of the compositions containing them can be substantially broadened and adapted to prevailing circumstances by adding other insecticides and/or acaricides. Suitable additives are, for example, representatives of the following classes of active ingredient: organophosphorus compounds, nitrophenols and derivatives thereof, formamidines, ureas, carbamates, pyrethroids, chlorinated hydrocarbons and Bacillus thuringiensis preparations.

The compounds of formula I are used as pesticides in unmodified form or, preferably, together with the adjuvants conventionally employed in the art of formulation, and are therefore formulated in known manner e.g. into emulsifiable concentrates, directly sprayable or dilutable solutions, dilute emulsions, wettable powders, soluble powders, dusts, granulates, and also encapsulations in e.g. polymer substances. As with the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula I or combinations thereof with other insecticides or acaricides and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders are normally natural mineral fillers, such as calcite, talcum, kaolin, montmorillonite or attapulgite. In order to improve the physical properties it is also possible to add highly dispersed silicic acids or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of granulated materials of inorganic or organic nature can be used, e.g. especially dolomite or pulverised plant residues.

Depending on the nature of the compound of formula I to be formulated, or on the nature of the combinations thereof with other insecticides or acaricides, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained e.g. from coconut oil or tall oil. Other suitable surfactants that may be mentioned are fatty acid methyltaurin salts and modified and unmodified phospholipids.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and generally contain a $C_8$-$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing about 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ethylammonium bromide.

The surfactants customarily employed in the art of formulation are described, inter alia, in the following publications:

"Mc Cutcheon's Detergents and Emulsifiers Annual" MC Publishing Corp., Ridgewood, New Jersey, 1979;

Dr. Helmut Stache "Tensid Taschenbuch", Carl Hanser Verlag, Munich/Vienna 1981.

The pesticidal compositions according to the invention usually contain 0.1 to 99%, preferably 0.1 to 95%, of a compound of formula I or combinations thereof with other insecticides or acaricides, 1 to 99.9% of a solid or liquid adjuvant, and 0 to 25%, preferably 0.1 to 20%, of a surfactant. Whereas commercial products will preferably be formulated as concentrates, the end user will normally employ dilute formulations containing substantially lower concentrations of active ingredient.

The compositions according to the invention may also contain further additives such as stabilisers, antifoams, viscosity regulators, binders and tackifiers as well as fertilisers or other active ingredients for obtaining special effects.

EXAMPLES:

1. Preparation of the compounds of formula I and their intermediates

Example P.1:
2-oxo-5-trifluoromethyl-2,3-dihydro-1,3,4-oxadiazol-3-acetone 15 g (0.5 mole) of 80% NaH dispersion in oil are washed free of oil with petroleum ether and added to 125 ml of DMF. 77 g (0.5 mole) of 5-trifluoromethyl-1,3,4-oxadiazol-2(3H)-one in 250 ml of DMF are added dropwise to this suspension over a period of 1 hour at room temperature and the batch is then stirred for 3 hours. 55.5 g (0.6 mole) of chloroacetone are then added and the reaction mixture is stirred for 16 hours at room temperature. After concentration by evaporation, 1000 ml of water are added to the residue and the solid precipitate is filtered off with suction and dried to give the title compound of formula

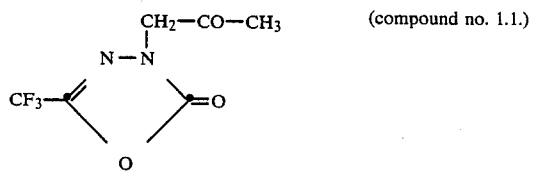

(compound no. 1.1.)

in the form of a colourless solid; m.p. 85° C.; yield: 96 g (91.7%).

The following compounds are prepared in an analogous manner:

TABLE 1

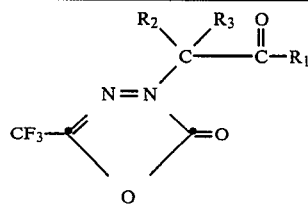

| Compound no. | $R_1$ | $R_2$ | $R_3$ | physic. data |
|---|---|---|---|---|
| 1.1 | $CH_3$ | H | H | m.p. 85° C. |
| 1.2 | i-$C_3H_7$ | H | H | m.p. 74–75° C. |
| 1.3 | $C(CH_3)_3$ | H | H | m.p. 67° C. |
| 1.4 | $C_6H_5$ | H | H | m.p. 100–102° C. |
| 1.5 | $CH_3$ | $CH_3$ | H | oil |
| 1.6 | $CH_3$ | $CH_3$ | $CH_3$ | oil |
| 1.7 | $C_2H_5$ | H | H | m.p. 76–77° C. |

TABLE 1-continued

| Compound no. | $R_1$ | $R_2$ | $R_3$ | physic. data |
|---|---|---|---|---|
| 1.8 | cyclopropyl | H | H | m.p. 77–78° C. |
|  | H | H | H |  |
|  | $C_2H_5$ | $CH_3$ | H |  |
|  | n-$C_3H_7$ | H | H |  |
|  | cyclopropyl | $CH_3$ | H |  |
|  | H | $CH_3$ | H |  |
|  | i-$C_3H_7$ | $CH_3$ | H |  |
|  | i-$C_3H_7$ | $CH_3$ | $CH_3$ |  |
|  | $C(CH_3)_3$ | $CH_3$ | H |  |
|  | $CH_3$ | $C_2H_5$ | H |  |
|  | $CH_3$ | $C_2H_5$ | $CH_3$ |  |
|  | cyclopropyl | $CH_3$ | $CH_3$ |  |
|  | cyclopropyl | $C_2H_5$ | $CH_3$ |  |

Example P.2:
2,3,4,5-tetrahydro-3-oxo-4-amino-6-methyl-1,2,4-triazine 210 g (1.0 mole) of 2-oxo-5-trifluoromethyl-2,3-dihydro-1,3,4-oxadiazol-3-acetone are introduced, with cooling, into 250 ml of hydrazine hydrate. The resulting clear brown solution is concentrated by evaporation in vacuo after being stirred for 2 hours and the residue is chromatographed on silica gel (methylene chloride/methanol 9:1). The solvent is evaporated off and the title compound of formula

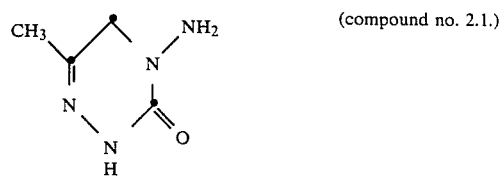

(compound no. 2.1.)

crystallises from the resulting oil after the addition of ether: m.p. 117°–119° C.; yield: 64 g (50%).

The following compounds are prepared in an analogous manner:

TABLE 2

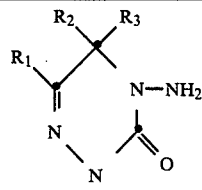

| Compound no. | R₁ | R₂ | R₃ | m.p. °C |
|---|---|---|---|---|
| 2.1 | CH$_3$ | H | H | 117–119 |
| 2.2 | CH$_3$ | CH$_3$ | H | 172–174 |
| 2.3 | CH$_3$ | CH$_3$ | CH$_3$ | 138–139 |
| 2.4 | C$_2$H$_5$ | H | H | 143–145 |
| 2.5 | i-C$_3$H$_7$ | H | H | 79–81 |
| 2.6 | C(CH$_3$)$_3$ | H | H | 148–150 |
| 2.7 | △ | H | H | 94–95 |
| 2.8 | C$_6$H$_5$ | H | H | 199–202 |
| 2.9 | 4-Cl—C$_6$H$_4$ | H | H | 208–210 |
|  | H | H | H |  |
|  | CH$_3$ | C$_2$H$_5$ | H |  |
|  | C$_2$H$_5$ | CH$_3$ | CH$_3$ |  |
|  | C$_2$H$_5$ | CH$_3$ | H |  |
|  | n-C$_3$H$_7$ | H | H |  |
|  | n-C$_3$H$_7$ | CH$_3$ | H |  |
|  | n-C$_3$H$_7$ | CH$_3$ | CH$_3$ |  |
|  | i-C$_3$H$_7$ | CH$_3$ | H |  |
|  | C(CH$_3$)$_3$ | CH$_3$ | H |  |
|  | C(CH$_3$)$_3$ | CH$_3$ | CH$_3$ |  |
|  | △ | CH$_3$ | CH$_3$ |  |
|  | △ | CH$_3$ | H |  |

Example P.3:

2,3,4,5-tetrahydro-3-oxo-4-[(pyridin-3-yl)-methyleneamino]-6-methyl-1,2,4-triazine 26.8 g (0.25 mole) of pyridine-3-carbaldehyde and 1 drop of concentrated HCl are added at 60° C. to 32 g (0.25 mole) of 2,3,4,5-tetrahydro-3-oxo-4-amino-6-methyl-1,2,4-triazine dissolved in 250 ml of ethanol. After boiling for half an hour under reflux, the reaction mixture is cooled and the solid portion is isolated by filtration, washed with ether and dried to give the title compound of formula

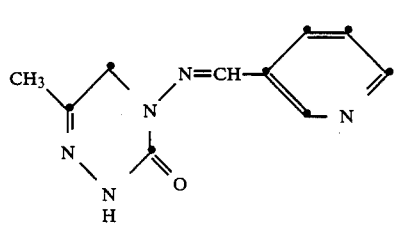

(compound no. 3.1)

in the form of a colourless solid; m.p. 227°–228° C.; yield: 48 g (90%).

The following compounds are prepared in an analogous manner:

TABLE 3

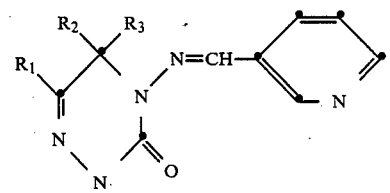

| Compound no. | R₁ | R₂ | R₃ | physical data |
|---|---|---|---|---|
| 3.1 | CH$_3$ | H | H | m.p. 227–228° C. |
| 3.2 | CH$_3$ | CH$_3$ | H | m.p. 139–141° C. |
| 3.3 | CH$_3$ | CH$_3$ | CH$_3$ | m.p. 158° C. |
| 3.4 | C$_2$H$_5$ | H | H | m.p. 223–224° C. |
| 3.5 | i-C$_3$H$_7$ | H | H | m.p. 201–203° C. |
| 3.6 | △ | H | H | m.p. 243–244° C. |
| 3.7 | C(CH$_3$)$_3$ | H | H | m.p. 195–196° C. |
| 3.8 | C$_6$H$_5$ | H | H | m.p. 263–264° C. |
| 3.9 | 4-Cl—C$_6$H$_4$ | H | H | m.p. 246–247° C. |
|  | H | H | H |  |
|  | H | CH$_3$ | H |  |
|  | H | CH$_3$ | CH$_3$ |  |
|  | CH$_3$ | C$_2$H$_5$ | H |  |
|  | CH$_3$ | C$_2$H$_5$ | CH$_3$ |  |
|  | CH$_3$ | C$_2$H$_5$ | C$_2$H$_5$ |  |
|  | C$_2$H$_5$ | CH$_3$ | H |  |
|  | C$_2$H$_5$ | CH$_3$ | CH$_3$ |  |
|  | C$_2$H$_5$ | C$_2$H$_5$ | H |  |
|  | n-C$_3$H$_7$ | H | H |  |
|  | n-C$_3$H$_7$ | CH$_3$ | H |  |
|  | n-C$_3$H$_7$ | CH$_3$ | CH$_3$ |  |
|  | n-C$_3$H$_7$ | C$_2$H$_5$ | CH$_3$ |  |
|  | i-C$_3$H$_7$ | CH$_3$ | H |  |
|  | i-C$_3$H$_7$ | CH$_3$ | CH$_3$ |  |
|  | △ | CH$_3$ | H |  |
|  | △ | CH$_3$ | CH$_3$ |  |
|  | C(CH$_3$)$_3$ | CH$_3$ | H |  |
|  | C(CH$_3$)$_3$ | CH$_3$ | CH$_3$ |  |
|  | n-C$_4$H$_9$ | H | H |  |
|  | C$_6$H$_5$ | CH$_3$ | H |  |
|  | C$_6$H$_5$ | CH$_3$ | CH$_3$ |  |

Example P.4:

2,3,4,5-tetrahydro-3-oxo-[(pyridin-3-yl)-methylamino]-6-isopropyl-1,2,4-triazine 37.8 g (1 mole) of sodium borohydride are introduced in portions into a suspension of 24.5 g (0.1 mole) of 2,3,4,5-tetrahydro-3-oxo-4-[(pyridin-3-yl)-methyleneamino]-6-isopropyl-1,2,4-triazine in 800 ml of methanol; the reaction mixture is then stirred for a few hours at room temperature and then boiled under reflux for 12 hours. After evaporation of the solvent, the residue is stirred with acetonitrile and then filtration is carried out. After concentrating the acetonitrile solution by evaporation, the residue is stirred with ether and the crystallisate is isolated by filtration to give the title compound of formula

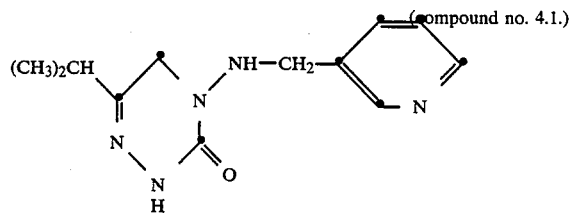

(compound no. 4.1.)

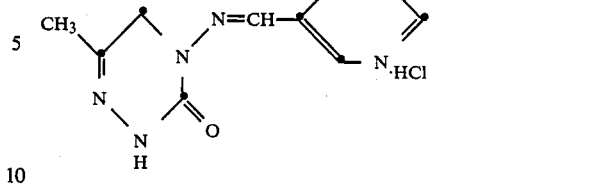

(compound no. 5.1.)

in the form of a colourless crystal powder; m.p. 105°-107° C.; yield: 12 g (49%).

The following compounds are prepared in an analogous manner:

TABLE 4

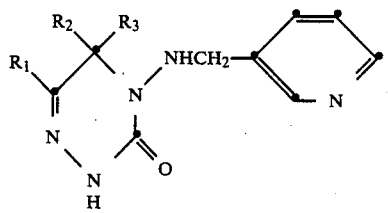

| Compound no. | R$_1$ | R$_2$ | R$_3$ | physical data |
|---|---|---|---|---|
| 4.1 | i-C$_3$H$_7$ | H | H | m.p. 105-107° C. |
| 4.2 | CH$_3$ | H | H | m.p. 161-163° C. |
| 4.3 | C(CH$_3$)$_3$ | H | H | m.p. 162-164° C. |
| 4.4 | C$_2$H$_5$ | H | H | m.p. 94-96° C. |
| 4.5 | △ | H | H | m.p. 133-135° C. |
| 4.6 | CH$_3$ | CH$_3$ | H | m.p. 35° C. |
| 4.7 | CH$_3$ | CH$_3$ | CH$_3$ | m.p. 150° C. |
| | H | H | H | |
| | H | CH$_3$ | H | |
| | C$_2$H$_5$ | CH$_3$ | H | |
| | n-C$_3$H$_7$ | H | H | |
| | i-C$_3$H$_7$ | CH$_3$ | H | |
| | i-C$_3$H$_7$ | CH$_3$ | CH$_3$ | |
| | △ | CH$_3$ | H | |
| | △ | C$_2$H$_5$ | CH$_3$ | |
| | C(CH$_3$)$_3$ | CH$_3$ | H | |
| | C(CH$_3$)$_3$ | CH$_3$ | CH$_3$ | |
| | C(CH$_3$)$_3$ | C$_2$H$_5$ | H | |
| | C$_6$H$_5$ | H | H | |
| | C$_6$H$_5$ | CH$_3$ | H | |

Example P.5:

2,3,4,5-tetrahydro-3-oxo-4-[(pyridin-3-yl)-methyleneamino]-6-methyl-1,2,4-triazinehydrochloride 21.7 g of 2,3,4,5-tetrahydro-3-oxo-4-[(pyridin-3-yl)-methyleneamino]-6-methyl-1,2,4-triazine are dissolved, with heating, in 60 ml of 2N hydrochloric acid. The hot solution is filtered and cooled. The precipitate which crystallises out is isolated by filtration, washed with alcohol and ether and dried in vacuo to give the title compound of formula in the form of a colourless crystal powder; m.p. 240-241° C. with decomposition; yield: 19 g (75%).

The following compounds are prepared in an analogous manner:

TABLE 5

| Compound no. | R$_1$ | R$_2$ | R$_3$ | Z | Y$^\ominus$ | m.p. °C. |
|---|---|---|---|---|---|---|
| 5.1 | CH$_3$ | H | H | —N=CH— | Cl | 240-241 |
| 5.2 | CH$_3$ | H | H | —N=CH— | ½SO$_4$ | 237 |
| 5.3 | C$_2$H$_5$ | H | H | —N=CH— | Cl | 253 |
| 5.4 | C$_2$H$_5$ | H | H | —N=CH— | ½SO$_4$ | 205 |
| 5.5 | C$_2$H$_5$ | H | H | —N=CH— | NO$_3$ | 181 |
| 5.6 | CH$_3$ | H | H | —N=CH— | NO$_3$ | 177 |
| 5.7 | C$_2$H$_5$ | H | H | —N=CH— | CH$_3$SO$_3$ | 224-225 |
| 5.8 | CH$_3$ | H | H | —N=CH— | CF$_3$CO$_2$ | 196 |
| 5.9 | CH$_3$ | H | H | —N=CH— | ⅓PO$_4$ | 206-210 |
| 5.10 | CH$_3$ | H | H | —N=CH— | oxalic acid | 218-219 |
| 5.11 | (CH$_3$)$_3$C | H | H | —N=CH— | Cl | 229-230 |
| 5.12 | △ | H | H | —N=CH— | NO$_3$ | 229-230 |
| 5.13 | △ | H | H | —N=CH— | Cl | 250 |
| 5.14 | △ | H | H | —N=CH— | CF$_3$CO$_2$ | 196-198 |
| 5.15 | △ | H | H | —N=CH— | oxalic acid | 220 |
| 5.16 | △ | H | H | —N=CH— | ½SO$_4$ | 210 |
| 5.17 | △ | H | H | —N=CH— | ⅓PO$_4$ | 219 |

2. Formulation Examples

Formulations for active ingredients of formula I or combinations of these active ingredients with other insecticides or acaricides (throughout, percentages are by weight):

| F1. Wettable powders | (a) | (b) | (c) |
|---|---|---|---|
| active ingredient or combination | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |

| F1. Wettable powders | (a) | (b) | (c) |
|---|---|---|---|
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient or combination is mixed with the adjuvants and the mixture is thoroughly ground in a suitable mill, affording wettable powders which can be diluted with water to give suspensions of the desired concentration.

| F2. Emulsifiable concentrate | |
|---|---|
| active ingredient or combination | 10% |
| octylphenol polyethylene glycol ether (4-5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| F3. Dusts | (a) | (b) |
|---|---|---|
| active ingredient or combination | 5% | 8% |
| talcum | 95% | — |
| kaolin | — | 92% |

Ready-for-use dusts are obtained by mixing the active ingredient or combination with the carrier and grinding the mixture in a suitable mill.

| F4. Extruder granulate | |
|---|---|
| active ingredient or combination | 10% |
| sodium lignosulfonate | 2% |
| carboxymethylcellulose | 1% |
| kaolin | 87% |

The active ingredient or combination is mixed and ground with the adjuvants, and the mixture is subsequently moistened with water. The mixture is extruded, granulated and then dried in a stream of air.

| F5. Coated granulate | |
|---|---|
| active ingredient or combination | 3% |
| polyethylene glycol (mol. wt. 200) | 3% |
| kaolin | 94% |

The finely ground active ingredient or combination is uniformly applied, in a mixer, to the kaolin moistened with polyethylene glycol. Non-dusty coated granulates are obtained in this manner.

| F6. Suspension concentrate | |
|---|---|
| active ingredient or combination | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |

| F6. Suspension concentrate | |
|---|---|
| water | 32% |

The finely ground active ingredient or combination is intimately mixed with the adjuvants, giving a suspension concentrate from which suspensions of any desired concentration can be obtained by dilution with water.

3. Biological Examples

Example B.1: Action against *Aedes aegypti* (larvae)

A concentration of 400 ppm is obtained by pipetting a specific amount of a 0.1% solution of the test compound in acetone onto the surface of 150 ml of water in a container. After the acetone has evaporated, 30 to 40 two-day-old Aedes larvae are put into the container. Mortality counts are made after 2 and 7 days.

Compounds according to Examples P.3 to P.5 exhibit good activity in this test.

Example B.2: Contact action against *Aphis craccivora*

Before the start of the test, 4- to 5-day-old pea seedlings (*Vicia faba*) reared in pots are each populated with about 200 insects of the species Aphis craccivora. The treated plants are sprayed direct to drip point 24 hours later with an aqueous formulation containing 12.5 ppm of the test compound. Two plants are used for each test compound, and a mortality count is made after a further 24 and 72 hours. The test is carried out at 21°-22° C. and a relative humidity of about 55%.

Compounds according to Examples P.3 to P.5 exhibit good activity in this test.

Example B.3: Systemic action against *Aphis craccivora*

Rooted bean plants are transplanted into pots containing 600 ccm of soil. 50 ml of a formulation (prepared from a 25% wettable powder) of the test compound in a concentration of 400 ppm are then poured directly onto the soil in each pot.

After 24 hours the growing parts of the plants are populated with aphids of the species *Aphis craccivora* and a plastic cylinder is then slipped over the plants to protect the aphids from any possible contact with the test substance either directly or via the gas phase.

A mortality count is made 48 and 72 hours after the start of the test. Two plants, each in a separate pot, are used for each test substance. The test is carried out at 25° C. and about 70% relative humidity.

Compounds according to Examples P.3 to P.5 exhibit good activity in this test.

Example B.4: Contact action against *Myzus persicae*, direct spray test 4 days before treatment, peperoni plants (in the 6-leaf stage, in pots) are infested with a population of *Myzus persicae* (R strain) by placing pea seedlings 2-3 cm long and well populated with aphids on the peperoni plants. As soon as the pea seedlings begin to dry up, the aphids migrate onto the test plants (peperoni). 24 hours later, the treated plants are sprayed direct to drip point with an aqueous suspension, prepared from a 25% wettable powder, containing 100 ppm of the test compound. Four plants are used for each test substance. A mortality count is made 7 days after application. The test is carried out at 21°-22° C. and about 60% relative humidity.

The compounds according to Examples P.3 to P.5 exhibit 80-100% mortality in this test.

Example B.5: Test of long-term action against *Myzus persicae*

Peperoni plants (in the 6-leaf stage, in pots) are treated by spray application with the test solutions and, 2 days after the treatment, the test plants are infested with a population of *Myzus persicae* (R strain) as described in Example B.4. An evaluation of the percentage mortality is made 5 days after populating the plants.

The compounds according to Examples P.3 to P.5 exhibit 50-100% mortality at a concentration of 100 ppm.

What is claimed is:

1. A compound of formula I

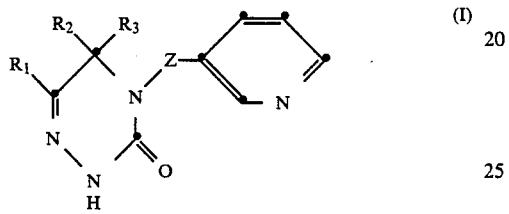

wherein
$R_1$ is hydrogen, $C_1-C_{12}$alkyl, $C_3-C_6$cycloalkyl, $C_1-C_4$-alkoxy-$C_1-C_6$alkyl, $C_1-C_2$haloalkyl, phenyl, benzyl, phenethyl, phenpropyl, phenbutyl or phenpentyl, or a phenyl, benzyl, phenethyl, phenpropyl, phenbutyl or phenpentyl radical that is mono- or di-substituted by halogen, $C_1-C_5$alkyl, $C_1-C_2$haloalkyl, methoxy and/or by ethoxy, $R_2$ is hydrogen, $C_1-C_6$alkyl or $C_3-C_6$cycloalkyl, or is phenyl that is unsubstituted or substituted by $C_1-C_{12}$alkyl, halogen or by $C_1-C_{12}$haloalkyl, or $R_1$ and $R_2$ together form a saturated or unsaturated 3- to 7-membered carbocycle,
$R_3$ is hydrogen or $C_1-C_6$alkyl and
Z is —N=CH— or —NH—$CH_2$—, or a salt thereof with an organic or inorganic acid.

2. A compound of claim 1, wherein $R_1$ is hydrogen, $C_1-C_6$alkyl, $C_3-C_5$cycloalkyl, phenyl or phenyl that is mono- or di-substituted by halogen, $C_1-C_3$alkyl, methoxy or by ethoxy; each of $R_2$ and $R_3$ is hydrogen or $C_1-C_4$alkyl and Z is —N=CH— or —NH—$CH_2$—.

3. A compound of claim 2, wherein $R_1$ is hydrogen, $C_1-C_4$alkyl, cyclopropyl or phenyl; $R_2$ is hydrogen, methyl or ethyl; $R_3$ is hydrogen or methyl; and Z is —N=CH—.

4. A compound of claim 2, wherein $R_1$ is hydrogen, $C_1-C_4$alkyl, cyclopropyl or phenyl; $R_2$ is hydrogen, methyl or ethyl; $R_3$ is hydrogen or methyl; and Z is —NH—$CH_2$—.

5. The compounds according to claim 3 of formulae

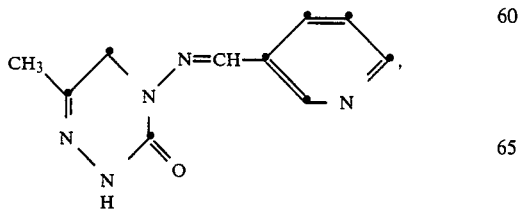

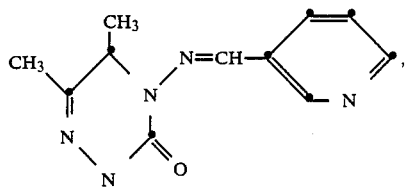

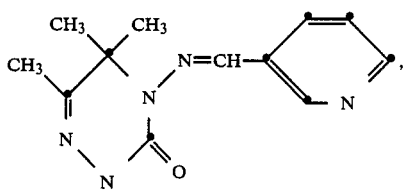

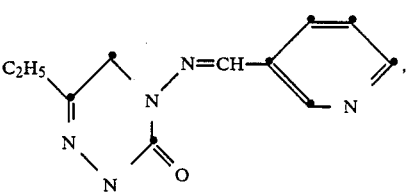

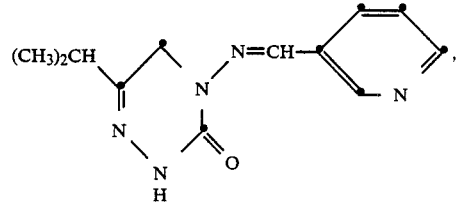

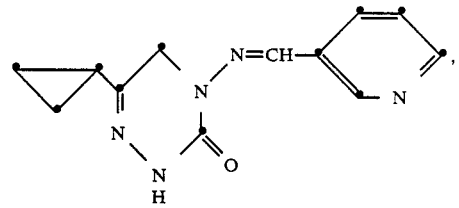

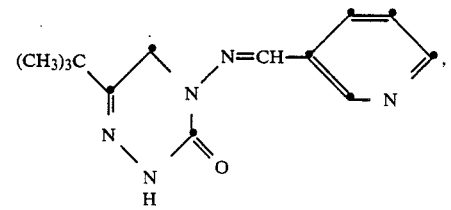

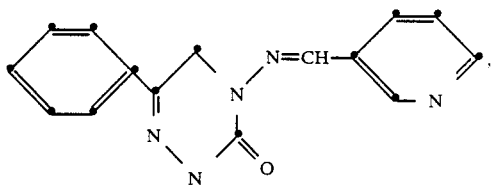

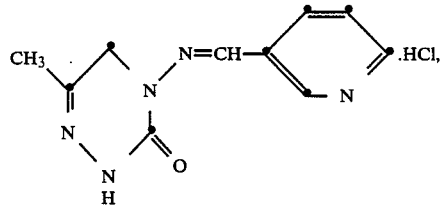
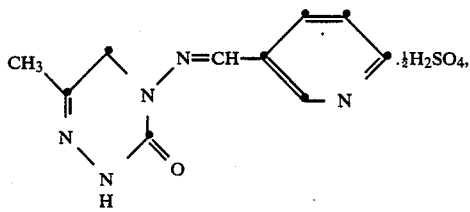
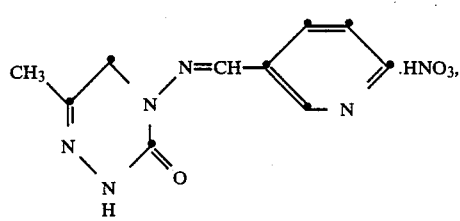
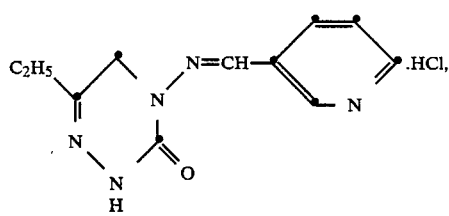
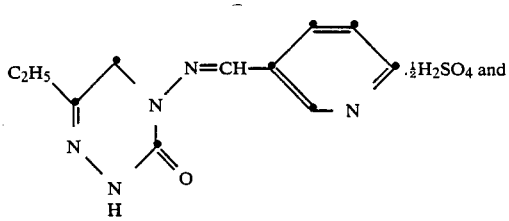
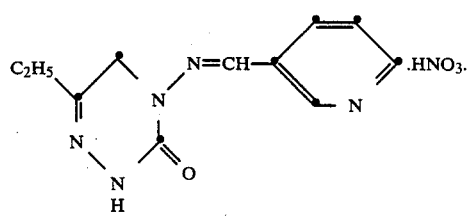

6. The compounds according to claim 4 of formulae

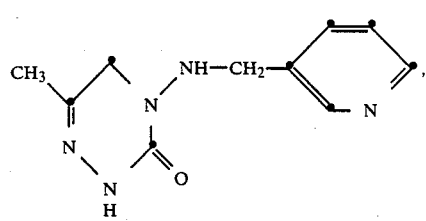

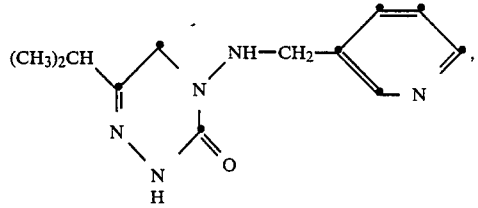
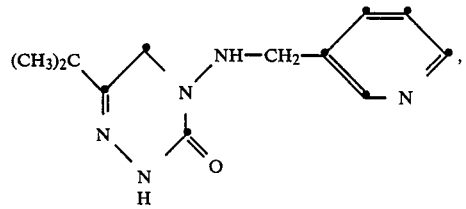
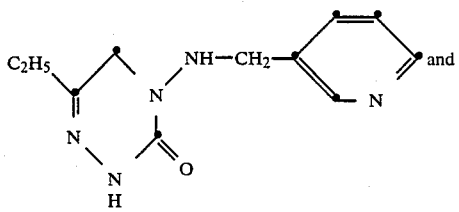
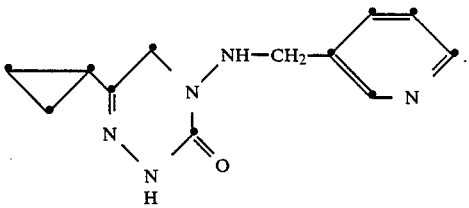

7. A composition for controlling insects and arachnids which contains as active component an effective amount of a compound of formula I

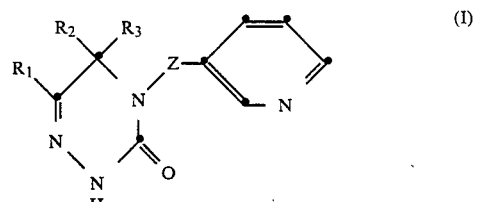

wherein $R_1$ is hydrogen, $C_1-C_{12}$alkyl, $C_3-C_6$cycloalkyl, $C_1-C_4$-alkoxy-$C_1-C_4$alkyl, $C_1-C_2$haloalkyl, phenyl, benzyl, phenethyl, phenpropyl, phenbutyl or phenpentyl, or a phenyl, benzyl, phenethyl, phenpropyl, phenbutyl or phenpentyl radical that is mono- or di-substituted by halogen, $C_1-C_5$alkyl, $C_1-C_2$haloalkyl, methoxy and/or by ethoxy, $R_2$ is hydrogen, $C_1-C_6$alkyl or $C_3-C_6$cycloalkyl, or is phenyl that is unsubstituted or substituted by $C_1-C_{12}$alkyl, halogen or by $C_1-C_{12}$haloalkyl, or $R_1$ and $R_2$ together form a saturated or unsaturated 3- to 7-membered carbocycle, $R_3$ is hydrogen or $C_1-C_6$alkyl and Z is —N=CH— or —NH—$CH_2$—, or a salt thereof with an organic or inorganic acid, together with suitable carriers and/or adjuvants.

8. A method of controlling pests selected from insects and arachids in and on animals and plants, which comprises bringing the pests in their various stages of development into contact with a compound of formula I

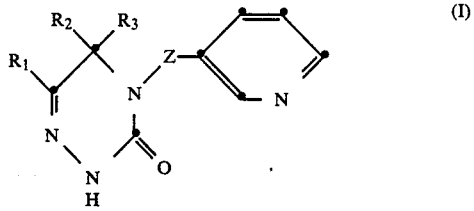

(I)

wherein $R_1$ is hydrogen, $C_1$-$C_{12}$alkyl, $C_3$-$C_6$cycloalkyl, $C_1$-$C_4$alkoxy-$C_1$-$C_6$alkyl, $C_1$-$C_2$haloalkyl, phenyl, benzyl, phenethyl, phenpropyl, phenbutyl or phenpentyl, or a phenyl, benzyl, phenethyl, phenpropyl, phenbutyl or phenpentyl radical that is mono- di-substituted by halogen, $C_1$-$C_5$alkyl, $C_1$-$C_2$haloalkyl, methoxy and/or by ethoxy, $R_2$ is hydrogen, $C_1$-$C_6$alkyl or $C_3$-$C_6$cycloalkyl, or is phenyl that is unsubstituted or substituted by $C_1$-$C_{12}$alkyl, halogen or by $C_1$-$C_{12}$haloalkyl, or $R_1$ and $R_2$ together form a saturated or unsaturated 3- to 7-membered carbocycle, $R_3$ is hydrogen or $C_1$-$C_6$alkyl and Z is $-N=CH-$ or $-NH-CH_2-$, or with a salt thereof with an organic or inorganic acid.

9. A method of claim 8 for controlling plant-destructive insects.

10. A method of claim 9 for controlling sucking insects.

11. A compound of formula IIa

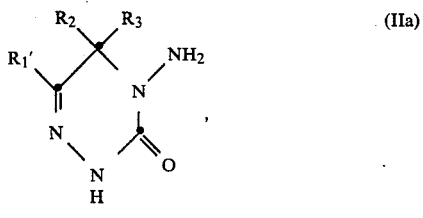

(IIa)

wherein $R_1'$ is hydrogen, $C_1$-$C_{12}$alkyl, $C_3$-$C_6$cycloalkyl, $C_1$-$C_4$alkoxy-$C_1$-$C_6$alkyl, $C_1$-$C_2$haloalkyl, benzyl, phenethyl, phenpropyl, phenbutyl or phenpentyl, or a phenyl, benzyl, phenethyl, phenpropyl, phenbutyl or phenpentyl radical that is mono- or di-substituted by halogen, $C_1$-$C_5$alkyl, $C_1$-$C_2$haloalkyl, methoxy and/or by ethoxy, $R_2$ is hydrogen, $C_1$-$C_6$alkyl or $C_3$-$C_6$cycloalkyl, or is phenyl that is unsubstituted or substituted by $C_1$-$C_{12}$alkyl, halogen or by $C_1$-$C_{12}$haloalkyl, or $R_1'$ and $R_2$ together form a saturated or unsaturated 3- to 7-membered carbocycle, and $R_3$ is hydrogen or $C_1$-$C_6$alkyl.

12. A compound of claim 11, wherein $R_1'$ is hydrogen, $C_1$-$C_6$alkyl or $C_3$-$C_5$cycloalkyl, or phenyl that is mono- or di-substituted by halogen, $C_1$-$C_3$alkyl, methoxy or by ethoxy; and each of $R_2$ and $R_3$ is hydrogen or $C_1$-$C_4$alkyl.

13. A compound of claim 12, wherein $R_1'$ is hydrogen, $C_1$-$C_4$alkyl or cyclopropyl; $R_2$ is hydrogen, methyl or ethyl; and $R_3$ is hydrogen or methyl.

14. A compound of claim 13 of formulae

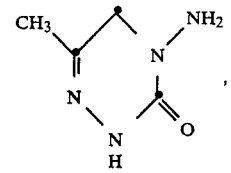

,

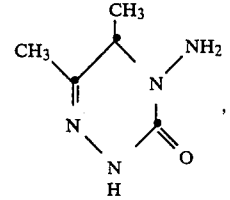

,

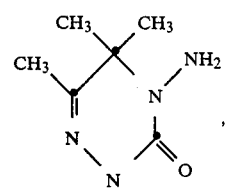

,

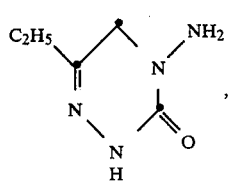

,

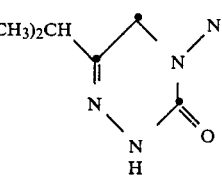

,

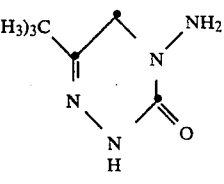

and

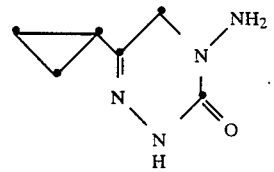

* * * * *